United States Patent [19]

Bauman

[11] Patent Number: 4,607,623
[45] Date of Patent: Aug. 26, 1986

[54] UNITARY INSERT SUPPORT FRAME FOR THE HANDLE OF AN EXAMINING DEVICE

[76] Inventor: Jack Bauman, 1677 San Onofre Dr., Pacific Palisades, Calif. 90272

[21] Appl. No.: 669,473

[22] Filed: Nov. 8, 1984

[51] Int. Cl.⁴ .............................................. A61B 1/26
[52] U.S. Cl. ..................................... 128/11; 362/217; 362/362; 362/804
[58] Field of Search ...................... 128/11, 6; 362/202, 362/205, 208, 217, 362, 804

[56] References Cited

U.S. PATENT DOCUMENTS

| | | | |
|---|---|---|---|
| 2,778,267 | 1/1957 | Miller, Jr. | 128/6 X |
| 3,426,749 | 2/1969 | Jephcott | 128/11 |
| 3,598,113 | 8/1971 | Moore | 128/11 |
| 3,766,909 | 10/1973 | Ozbey | 128/11 |
| 3,771,514 | 11/1973 | Huffman et al. | 128/11 |
| 3,826,248 | 7/1974 | Gobels | 128/11 |
| 4,037,588 | 7/1977 | Heckele | 128/11 |
| 4,114,609 | 9/1977 | Moses | 128/11 |
| 4,273,112 | 6/1981 | Heine et al. | 128/11 |
| 4,295,465 | 10/1981 | Racz et al. | 128/11 |
| 4,306,547 | 12/1981 | Lowell | 128/11 |
| 4,320,745 | 3/1982 | Bhitiyakul et al. | 128/11 |

*Primary Examiner*—William H. Grieb
*Attorney, Agent, or Firm*—Fulwider, Patton, Rieber, Lee & Utecht

[57] ABSTRACT

The invention is directed to an improved support frame for use in the handle of an examining device, such as a laryngoscope, which supports and provides electrical conduction for the batteries and the light source and, in a preferred embodiment, also includes a light switch and a reflector.

12 Claims, 6 Drawing Figures

U.S. Patent     Aug. 26, 1986     4,607,623
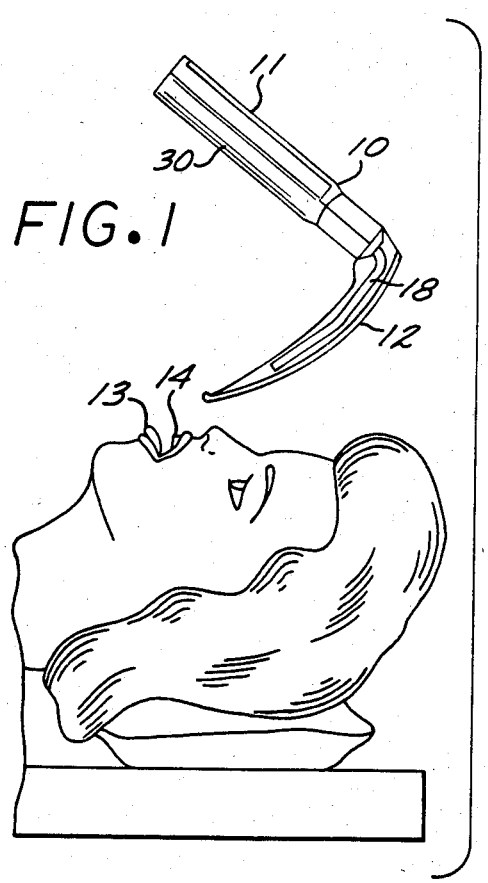
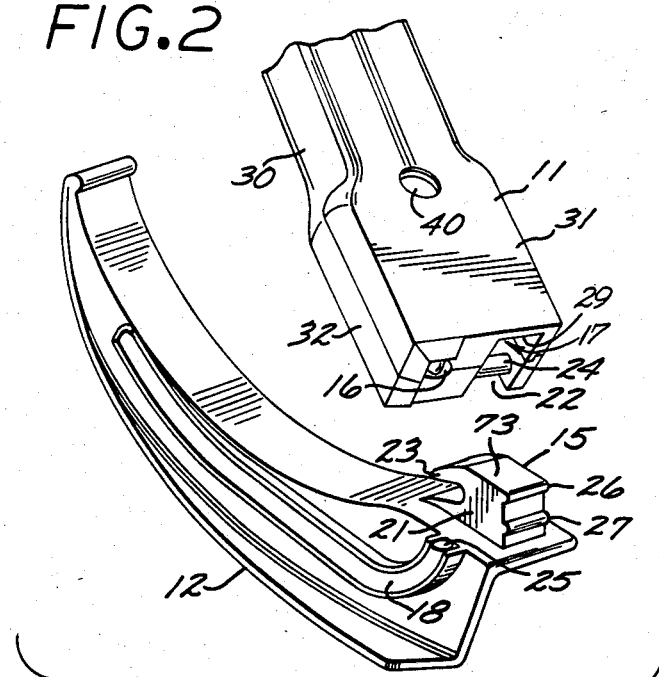
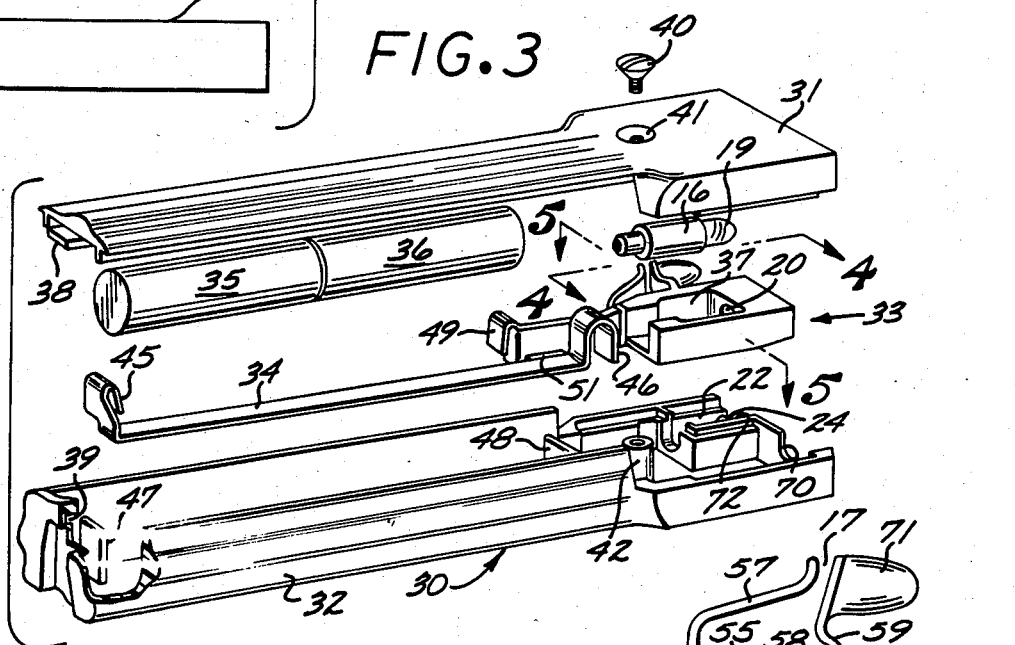
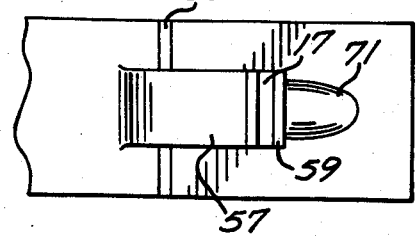
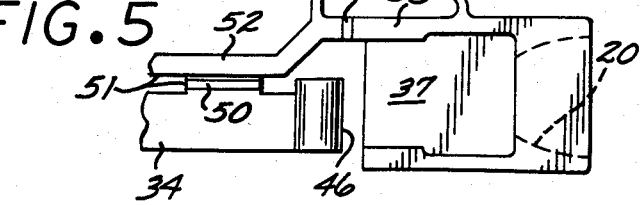
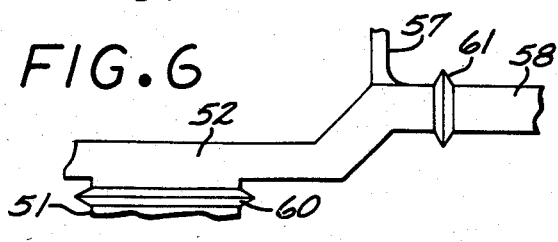

UNITARY INSERT SUPPORT FRAME FOR THE HANDLE OF AN EXAMINING DEVICE

BACKGROUND OF THE INVENTION

This invention generally relates to examination devices, such as laryngoscopes and specula of various types, and particularly to an improved handle therefor having a unitary insert support frame adapted to support the battery package and the light source and also to form the electrical switch for energizing the light source and a reflector.

Laryngoscopes generally comprise a blade and a cooperating handle which are connected together in an L-shaped configuration. The handle normally serves as an enclosure for one or more batteries which energize a light source in the top of the handle. The switch for energizing the light source is usually also positioned at the top of the handle immediately adjacent to the light source and is activated by the blade when it is connected to the handle in an operative position. Light from the light source is directed to the proximal end of a light conductor disposed in or on the blade. Light passes through the light conductor to the distal end thereof to illuminate the field of view, such as a patient's mouth and larynx, during the examination thereof by medical personnel.

When using the device, the surface on the blade adjacent to the handle is used to press against the tongue and mandible of a patient in a supine position in order to prevent the patient's tongue from obstructing the view during the visual examination of the larynx. The opposite blade surface is positioned opposing the upper front teeth of the patient, which are occasionally used as a fulcrum to expose the larynx. While the instrument is useful in examining the larynx, the primary function of a laryngoscope is to expose the larynx in order to facilitate the insertion of an endotracheal tube into the trachea of the lungs usually to administer anesthetic gases therein.

The handle of the prior examining devices enclose one or more batteries in series, a light source and a switch therefor in a manner similar in some respects to a common flashlight. The interior of the handle body generally was provided with a plurality of inwardly projecting integral ribs which supported the battery package in a proper position for electrical contact. The electrical contacts with the batteries, at least one of which was usually spring actuated, were utilized to urge the terminals of the battery package into proper engagement with the electrical contacts. The negative terminal of the battery pack was electrically connected to the positive terminal of the light source, whereas the positive terminal of the battery pack was electrically connected to one terminal of the light switch. The other terminal of the light switch was electrically connected to the negative terminal of the light source. By activating the switch, the circuit was completed and the light source is thereby energized.

In many of the prior examining devices, the electrical connections usually involved extensive manual assembly if the connections were made by insulated wire or extended mechanical interconnection if the connections were made by solid uninsulated members. The manual assembly involved with the wire and the mechanical interconnections greatly increased the cost of the examining units.

Traditionally, examining devices such as laryngoscopes have been fabricated from metal components. In an effort to reduce the costs of these devices, many are now being made from impact resistant plastic materials such as acrylonitryle-butadiene-styrene polymers (ABS). Additionally the blades are usually disposable after use.

However, even with such cost reducing efforts, there still is a need to further reduce the cost of these examining devices, particularly the high cost of manufacturing the handle assembly. The present invention was developed to satisfy the need for reducing such costs and improve the function of such devices.

SUMMARY OF THE INVENTION

The present invention is directed to an improved handle assembly for examining devices such as laryngoscopes and particularly to a unitary support frame which is adapted to hold the battery package and light bulb and to form the light switch and reflector. Additionally, this unitary support structure is adapted to be readily inserted into and be secured within the interior chamber of the handle. The electrical connections between the batteries, the light reflector and the light switch, which activates the circuit, are formed integral with the support frame and at least at the electrical contact points, are on the surface of the support frame to facilitate electrical contact.

In a preferred embodiment electrical conducting material is fixed onto the surface of the support frame such as by plating and suitable discontinuities or electrical breaks are provided in the electrically conductive coating in order to electrically separate the light bulb, the light switch and the battery package so that current flows to energize the light bulb only when the contacts of the light switch are closed.

The light bulb is fitted into the reflector provided in the frame with an opening at the front thereof in order to allow light to pass from the light reflector to the light receiving face of a light conductor positioned adjacent to the light source on the blade. A reflector ensures proper optical coupling between the light bulb and the light conductor.

The unitary support frame is preferably manufactured from ABS resin by injection molding in a conventional fashion and then plated first with a conductive coating such as copper, aluminum, silver or tin then with a reflective coating such as aluminum, chromium, silver or nickel. It is preferred to have ridges at the points where discontinuities are necessary, so that after plating, the raised portion of the ridges can be removed thereby effecting the desired discontinuities in the plating and therby provide the electrical separation necessary for appropriate electrical current flow when the light switch is activated. Alternatively, the frame can be appropriately masked with a resist material prior to plating in order to maintain the electrical segregation necessary.

These and other advantages will become more apparent from the following detailed description, taken in conjunction with the accompanying drawings.

BRIEF DESCRIPTION OF THE DRAWINGS

FIG. 1 is a side elevational view of a laryngoscope preparatory to being used on a patient which embodies features of the invention;

FIG. 2 is an exploded in perspective view of the blade and handle of the laryngoscope shown in FIG. 1;

FIG. 3 is an exploded view in perspective illustrating a laryngoscope handle with a unitary insert support frame adapted to be secured in the handle;

FIG. 4 is a side view of the insert taken along the lines 4—4 shown in FIG. 3;

FIG. 5 is a top view of the insert taken along the lines 5—5 shown in FIG. 3; and FIG. 6 is an enlarged top view of the insert illustrating the ridges which are removed after plating.

In the drawings all corresponding parts are numbered the same.

DETAILED DESCRIPTION OF THE INVENTION

Reference is made to the drawings which illustrate a laryngoscope embodying features of the present invention. As shown in FIG. 1, laryngoscope 10, which generally comprises a handle 11 and a detachable blade 12, is utilized to depress a patient's tongue and mandible 13. The patient's front teeth 14 sometimes are used as a fulcrum for the blade 12 in order to more completely expose the patient's larynx during the examination. As shown in more detail in FIG. 2, the laryngoscope comprises a handle 11, a detachable blade 12 and means 15 to detachably secure blade 12 to the handle 11 into a general L-shaped configuration, a light bulb 16 and a light switch 17 to energize the light bulb 16 and a light conductor 18 in the blade 11. Light bulb 16 has a reflector 20 which is preferably eliptical as described in copending application Ser. No. 669,474 filed Nov. 8, 1984. As shown in FIG. 2, the blade 12 is attached to the handle 11 in a pivotal fashion by means 15 which includes an appendage 21. The appendage 21 is inserted into the open top channel 22 of the handle 11 with a pivotal motion so that the front end 23 of appendage 21 is hooked onto the pivot rod 24 provided in the channel 22 of the handle 11. The detents 26 and 27 engage a groove (not shown) in the back surface wall 29 of the channel 22 to urge the appendage 21 into a more firm engagement with pivot rod 24 and to thereby fix the blade 12 with respect to the handle 11 in a generally L-shaped configuration so that the light-receiving face 25 of light conductor 18 is in position adjacent the light bulb 16.

With particular reference to FIG. 3, the handle 11 includes a shell or housing 30 comprising a top section 31 which interfits with a bottom section 32. Also included is a unitary support frame 33 which is secured within the shell 30 and is adapted to support batteries 35 and 36 and is provided with a cavity 37 which is adapted to receive light bulb 19 and urge the bulb into the reflector 20. Shell 30 is formed by joining sections 31 and 32 at one end thereof by means of a finger extension 38 on section 31 which interfits into the slotted opening 39 in section 32 and on the other end thereof by means of a screw 40 which passes through the opening 41 in section 31 and which is threadably secured to the upstanding post 42 fixed to the interior of section 32.

Unitary support frame 33 is secured within the shell 30 by the back sides of electrical contact elements 45 and 46 thereof which snugly interfit with upstanding walls 47 and 48 respectively.

Means are provided integral with the unitary support frame 33 to conduct electrically between the batteries 35 and 36, the light switch 17 and the light bulb 16. Such electrical conducting means are on the surface of the support frame at least in those areas of the frame which function as electrical contact elements, such as contact elements 45, 46 and 49 and cavity 37. With the electrical conductors being integral with the support frame 33, the assembly of the device is highly simplified. The frame 33 is positioned on the bottom section 32; the batteries 35 and 36 and light bulb 16 are snapped into position and the top section 31 is put into position and secured there by means of screw 40. Thus, the assembly of the device requires essentially no mechanical skills and nothing more than a screwdriver.

Preferably, the surface of support frame 33 is provided with an electrically conducting coating such as copper, aluminum, silver or tin and then followed with a reflective coating of aluminum, silver or nickel. From a manufacturing standpoint, it has been found very economical to plate the entire frame 33 with such conductive and reflective coatings but provide discontinuities in the coating in certain areas in order to control the flow of electrical current in a desired manner. The discontinuities can be produced by having the desired areas coated with a resist material before applying the conductive coating or by mechanically or chemically removing the conductive coating from the desired areas after the conductive coating has been applied. Only the reflecting surface of reflector 20 needs a reflective surface.

With reference to FIG. 5, a first discontinuity 50 is provided on bridge 51 which connects beam 52 supporting electrical contact element 49 (shown in FIG. 3) with extension 34 of frame 33. Discontinuity 50 causes the electrical current to flow from the contact element 49 to arm 57 of the light switch 17. A second discontinuity 55 is provided on beam 58 between arms 57 and 59 of light switch 17 so that current flows through the switch 17 only when the ends of the two arms are in contact. The discontinuities must extend completely around the elements in order to block current flow. Also shown in FIG. 5 is cavity 37 which is adapted to receive the light bulb 19. Once positioned within the cavity, electrical contact element 46 urges the light bulb into an appropriate position within the reflector 20 which is preferably eliptical as described in copending application Ser. No. 669,474, filed Nov. 8, 1984.

In a preferred embodiment shown in FIG. 6 the support frame is formed with ridges 60 and 61 in those areas where the discontinuities are desired. After plating, the ridges are removed and with them the coating, thereby leaving the desired discontinuities 50 and 55.

When the support frame is secured within the housing 30, the light source 16 is in line with opening 70 provided in the housing 30. The push button 71 attached to flexible arm 59 of the light switch 17 projects through opening 72 provided in housing 30. In securing the blade 12 to the handle 11 in an operative position, the lower surface 73 of appendage 21 depresses push button 71, thereby actuating the switch 17.

Upon actuating switch 17, electrical current passes from the batteries 35 and 36 through contact element 49 and light switch 17 to the light bulb 16. The negative terminal of battery 35 is in contact with electrical contact element 45 which is electrically connected through conductive coating of extension 34 to electrical contact 49 which in turn is operatively connected to the light bulb 16 to thereby complete the circuit. The electrical contact elements 45, 49 and 46 are formed to resiliently engage their cooperative elements, namely, batteries 35 and 36 and light bulb 16, to ensure good electrical contact and to also provide physical support thereto.

The members of the examining device in accordance with the invention are preferably formed of an impact resistant thermoplastic material such as acrylonitrile-butadiene-styrene (ABS). The support frame 33 is preferably formed from a platable grade of ABS such as that sold under the trade name "Cyculac" by the Borg Warner Company and the part is very efficiently formed by injection molding.

The support frame can be readily plated by first applying a thin copper layer by electroless plating and then electrolytically plating another copper layer to form a conductive layer of about 0.5 to 2 mils (12.5–50 microns) thick. A thin reflective layer of aluminum about 0.01 to 0.1 mils (0.25–2.5 microns) thick is subsequently applied to the copper coating, preferably by vacuum deposition. Other conductive and reflective coatings of the same approximate thickness can also be utilized as previously discussed.

The aluminum layer provides improved corrosion resistance to the frame and also forms the reflective surface of the reflector 20. A much better bond can be obtained between the ABS substrate and the initial electroless copper strike if the ABS substrate is first etched in acid to roughen the surface thereof.

When the support frame is provided with the conductive elements integral with the frame in accordance with the invention, the manufacturing costs of the resultant examining device can be substantially reduced. Moreover, because of its simplicity, the reliability and durability of the product is excellent.

While the specific embodiment described herein has been limited to laryngoscopes, the invention can be applied to a wide variety of examining devices and other devices which assist in the observation of a field of view. Moreover, modifications and improvements can be made to the invention without departing from the inventive concepts thereof.

I claim:

1. A light generation device to facilitate observation of a field of view comprising:
   a. an elongated, hollow housing having an interior chamber with a first opening for discharging light and a second opening to accomodate a projecting element which activates a light switch;
   b. a unitary support frame having a battery section adapted to hold one or more batteries, a light section having a reflector, a light bulb disposed within the reflector and in optical communication with the first opening, and a light switch which is activated by means of an activating element projecting through the second opening, and means to secure the unitary support frame within the interior of the housing; and
   c. electrical conducting means integral with the unitary support frame and in electrical contact with the one or more batteries held in the battery section, the light bulb and the light switch to pass electrical current therebetween when the light switch is activated.

2. The light generation device of claim 1 wherein the electrical conducting means is a conductive metallic layer on the surface of the unitary support frame.

3. The light generation device of claim 2 wherein discontinuities are provided in the metallic layer on the surface of the unitary support frame in order to electrically segregate portions thereof to cause electrical current to flow to the light bulb to thereby energize the light source when the light bulb is activated.

4. The light generation device of claim 2 wherein the conductive layer is plated onto the unitary support frame.

5. The light generation device of claim 4 wherein the metallic layer plated onto the surface of the support frame comprises two layers, an initial layer from about 0.5 to about 2 mils thick of a conductive metal selected from the group consisting of copper, aluminum, tin and silver and a second layer from about 0.01 to about 0.10 mils thick of a reflective metal selected from the group consisting of aluminum, chromium and silver.

6. The light generation device of claim 2 wherein the unitary frame is formed by injection molding acrylonitrile-butadiene-styrene polymer.

7. An examining device comprising a handle which incorporates the light generation device of claim 1, a blade, means to detachably secure the blade to the handle in a generally L-shaped configuration, the light bulb in the handle optically coupled to a light conductor associated with the blade to direct light from the light bulb through the light conductor to a field of view and the reflector formed integral with the support frame to reflect light from the light bulb to the light conductor associated with the blade.

8. The examining device of claim 7 wherein the electrical conducting means integral with the unitary support frame comprises a conductive metallic layer which has been plated onto the support frame.

9. The examining device of claim 8 wherein discontinuities are provided in the conductive metallic layer on the surface of the unitary support frame in order to electrically segregate portions thereof to thereby cause electrical current to flow to the light bulb to thereby energize the light bulb when the light switch is activated.

10. The examining device of claim 9 wherein the light switch comprises two normally separated, electrically conductive arms supported from an electrically conductive element of the support frame which has a discontinuity between the two arms to electrically segregate the arms so that electricity will flow only when the two arms are brought into contact.

11. The examining device of claim 8 wherein a reflective metallic layer covers the conductive metallic layer at least in the reflector.

12. The examining device of claim 7 wherein the device is a laryngoscope.

* * * * *